(12) United States Patent
Utsunomiya

(10) Patent No.: US 7,869,045 B1
(45) Date of Patent: Jan. 11, 2011

(54) TARGET SUBSTANCE DETECTION SYSTEM

(75) Inventor: Norihiko Utsunomiya, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 972 days.

(21) Appl. No.: 11/686,066

(22) Filed: Mar. 14, 2007

(30) Foreign Application Priority Data

Mar. 22, 2006 (JP) .............................. 2006-078793

(51) Int. Cl.
*G01N 21/55* (2006.01)
(52) U.S. Cl. ...................................... 356/445; 356/448
(58) Field of Classification Search ......... 356/445–448, 356/450–458
See application file for complete search history.

(56) References Cited

U.S. PATENT DOCUMENTS 6,400,838 B2 *  6/2002  Watanabe ................... 382/144
6,421,128 B1 *  7/2002  Salamon et al. ............. 356/445
7,102,753 B2 *  9/2006  Kawate ....................... 356/445

OTHER PUBLICATIONS

Amanda J. Haes, et al., "A Localized Surface Plasmon Resonance Biosensor: First Steps toward an Assay for Alzheimer's Disease", Nano Lett, vol. 4, No. 6, May 2004, pp. 1029-1034.

\* cited by examiner

*Primary Examiner*—Gregory J Toatley
*Assistant Examiner*—Jarreas C Underwood
(74) *Attorney, Agent, or Firm*—Fitzpatrick, Cella, Harper & Scinto

(57) ABSTRACT

In a localized surface plasmon detection system using a metal thin film pattern, by radiating light for detection on a detecting element using an effective light source which has a peak out of an axis, the present invention strikes a balance between narrowing a peak width of a spectrum and highly efficient illumination even if it is a case of using converging or diffused light.

4 Claims, 7 Drawing Sheets

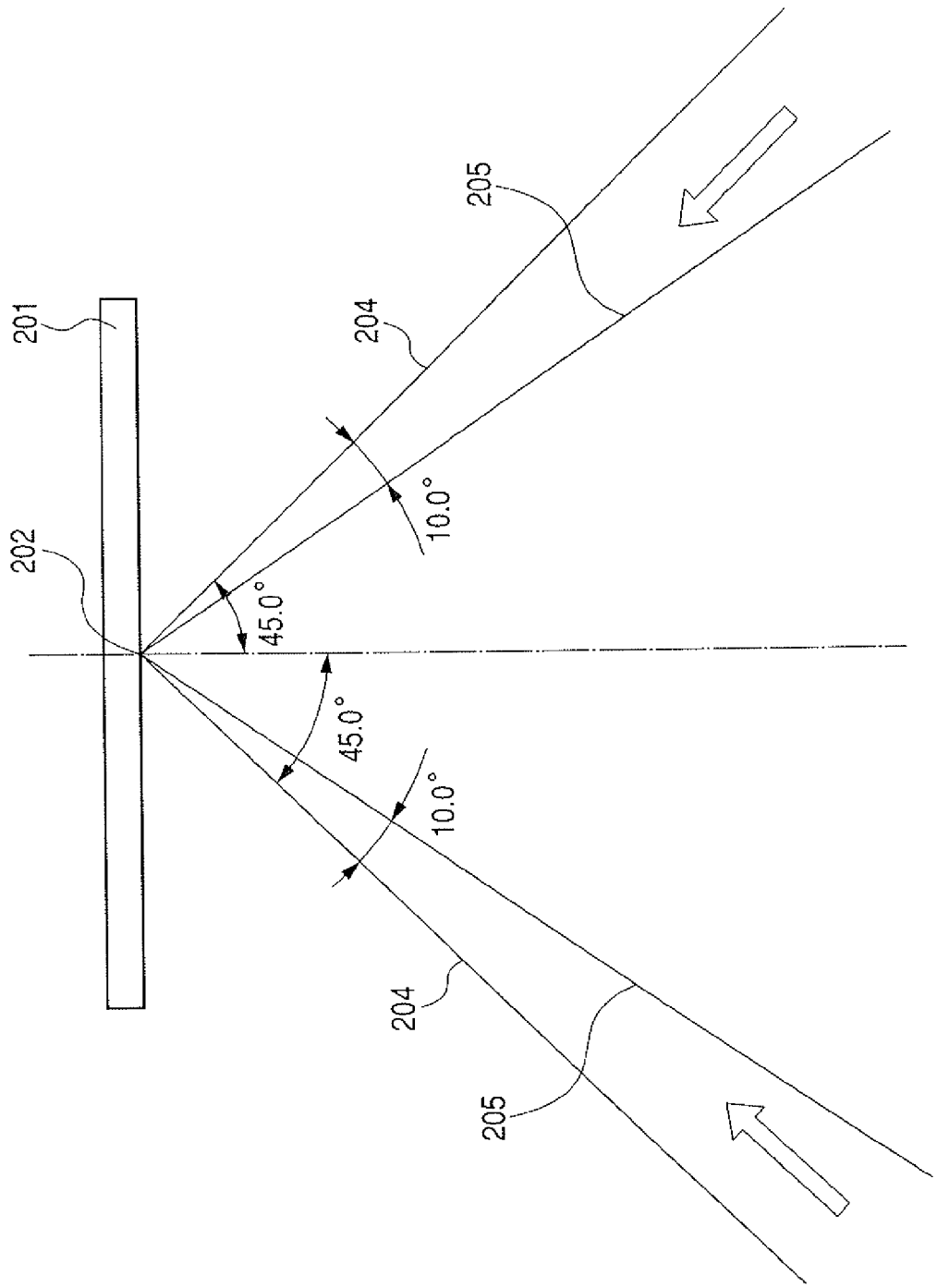

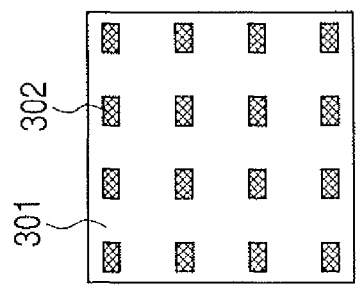
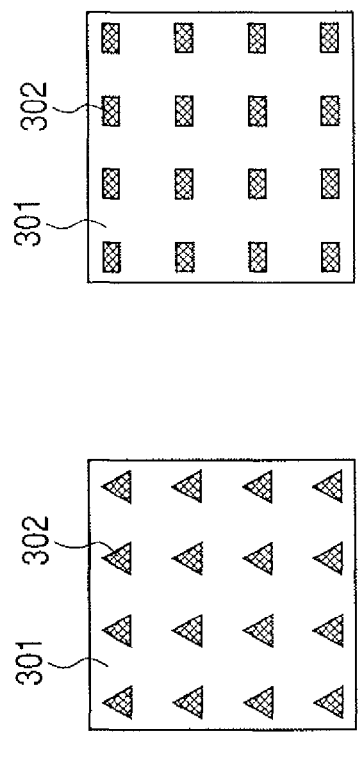
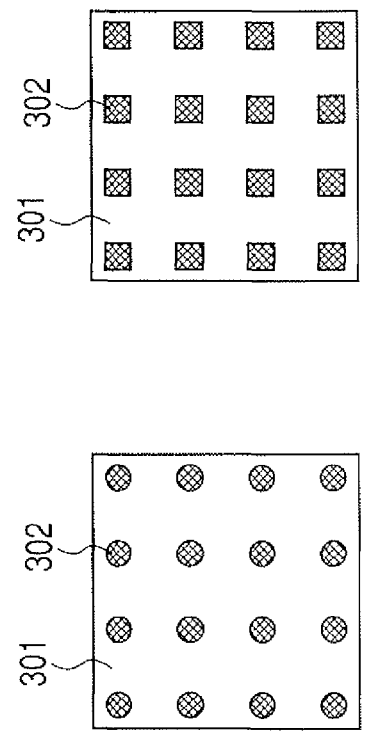
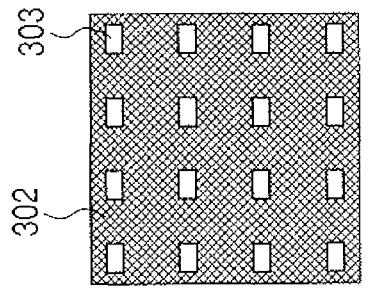
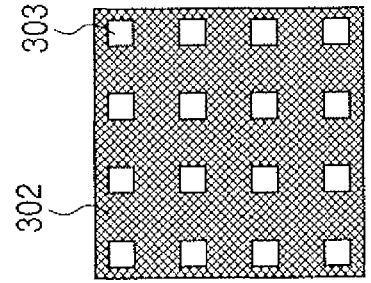
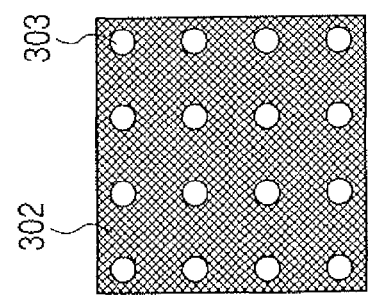

TARGET SUBSTANCE DETECTION SYSTEM

BACKGROUND OF THE INVENTION

1. Field of the Invention

The present invention relates to a target substance detection system which has a detecting element where a metallic pattern is arranged on a substrate so as to detect trace of target substance in a sample using plasmon resonance, and a target substance detecting apparatus for measuring a capture amount of target substance to the detecting element. In particular, the present invention relates to a target substance detection system which has a detecting element which captures a target substance using a capturing body which recognizes a target substance specifically, and a target substance detecting apparatus which measures optically an amount of the target substance captured by the detecting element using a wide band of optical irradiation.

2. Description of the Related Art

Up to now, a measuring method of immobilizing metal nanoparticles on a substrate surface, and detecting a substance near the metal nanoparticles using localized surface plasmon resonance induced there is known. When light is incident into metal nanoparticles, such as gold and silver, a characteristic resonance spectrum appears by the localized surface plasmon resonance. Its resonance wavelength is dependent on a dielectric constant of a solvent near the metal nanoparticles. As the dielectric constant becomes large, absorbance of a resonance peak becomes large and is shifted to a long wavelength side.

In Nano Lett., Vol. 4, No. 6, 2004 1029-1034, construction of an element of aiming at enhancement in detection capability by giving a feature of triangular disk structure to a form itself of each silver particulate used for an element is exemplified.

In addition, a biosensor to which plasmon resonance is applicable is a measuring device using excellent biomolecule recognition ability which an organism and a biomolecule have, and is expected recently for broad applications to various analyses in not only a medical field but also environments, food stuffs, and the like.

Nevertheless, in order to draw out performance of a sensor element using plasmon resonance, it is necessary to catch sharply an optical change of the sensor element, that is, a change of an absorbance peak. A proposal of an optical system for that has not been known yet.

SUMMARY OF THE INVENTION

A task which the present invention solves is to strike a balance between preventing dulling of a transmission or absorption peak generated due to the fact that light which is incident into a sensor element has a broad angle, and light use efficiency in a plasmon resonance sensor using a metal thin film pattern.

The present invention is directed to a target substance detection system for detecting a target substance in a sample, comprising:

(1) a detecting element for detecting a target substance which is comprised of:
a substrate optically transparent,
a metal thin film pattern formed on the substrate, and
a target substance capturing body immobilized on the metal thin film pattern; and (2) a target substance detecting apparatus which is comprised of:
an illumination optical system for irradiating the detecting element with a wideband detection light comprised of an effective light source which has a center of a strength peak out of an axis, a light receiving optical system which condenses light passed through the detecting element when the detecting element is irradiated with the detection light,
a unit for taking a spectrometric measurement of light condensed by the light receiving optical system,
a unit for bring a sample into contact with the detecting element, and
a unit for computing an amount of the target substances captured on the detecting element from a difference between spectroscopic properties before and after the contact of the sample with the detecting element.

In the target detection system, a form of the effective light source can have the same anisotropy as the anisotropy of the metal thin film pattern.

In the target detection system, a form of the effective light source can be made to be changeable at any time according to the anisotropy of the metal thin film pattern.

In the target detection system, an incident angle of light which is incident into the detecting element from a position most apart from an optical axis center in a distribution of the effective light source is a total reflection angle on the substrate.

According to the target substance detection system of the present invention, further enhancement in detection accuracy of a target substance using localized surface plasmon resonance can be achieved by using a wide band of light from an effective light source, which has a peak besides an axial center, as detection light.

Further features of the present invention will become apparent from the following description of exemplary embodiments with reference to the attached drawings.

BRIEF DESCRIPTION OF THE DRAWINGS

FIG. 3 is a principle explanatory diagram of a case of applying the present invention.

FIGS. 4A, 4B, 4C, 4D, 4E, 4F, 4G and 4H include examples of metal thin film patterns of a detecting element which can be used for the present invention.

DESCRIPTION OF THE EMBODIMENTS

A target substance detection system of the present invention includes at least a detecting element and an apparatus which detects a target substance by a plasmon resonating method.

The detecting element includes an optically transparent substrate, a metal thin film pattern formed on the substrate, and a target substance capturing body immobilized on the metal thin film pattern. In addition, the target substance detecting apparatus includes at least the following respective components.

i) An illumination optical system which includes an effective light source which is for radiating a wide band of detection light on the detecting element and has a center of a strength peak out of an axis ii) A light receiving optical system which condenses light, which transmits the detecting element, at the time of irradiation of detection light to the detecting element iii) A unit which performs spectroscopic measurement of light condensed by the light receiving optical system iv) A unit which contacts a sample with the detecting element v) A unit which acquires respectively spectroscopic characteristics before and after contact of the sample with the detecting element by a spectrum unit vi) A unit which calculates an amount of target substances captured on the detecting element from a change of spectroscopic characteristics before and after contact of the sample with the detecting element According to the system according to the present invention, an effect of obtaining further enhancement in the measurement accuracy can be obtained by using an effective light source, which has a strength center in a position which is apart from an optical axis center, as a light source of detection light, which is incident into a plasmon sensor using a metal thin film pattern. In consequence, the task cited previously is solved. In addition, the present invention is applicable to not only a sensor using so-called surface plasmon polariton, but also a sensor using localization surface plasmon polariton.

The illumination optical system in the system of the present invention has structure of not only narrowing an incident angle range to a detecting element, but also enabling an area of an effective light source to be taken widely by having a strength center out of an axis. Therefore, in comparison with a case that has a strength center on an axis, light use efficiency becomes high. Thereby, the above-mentioned effect of the present invention can be obtained.

Figure 2:
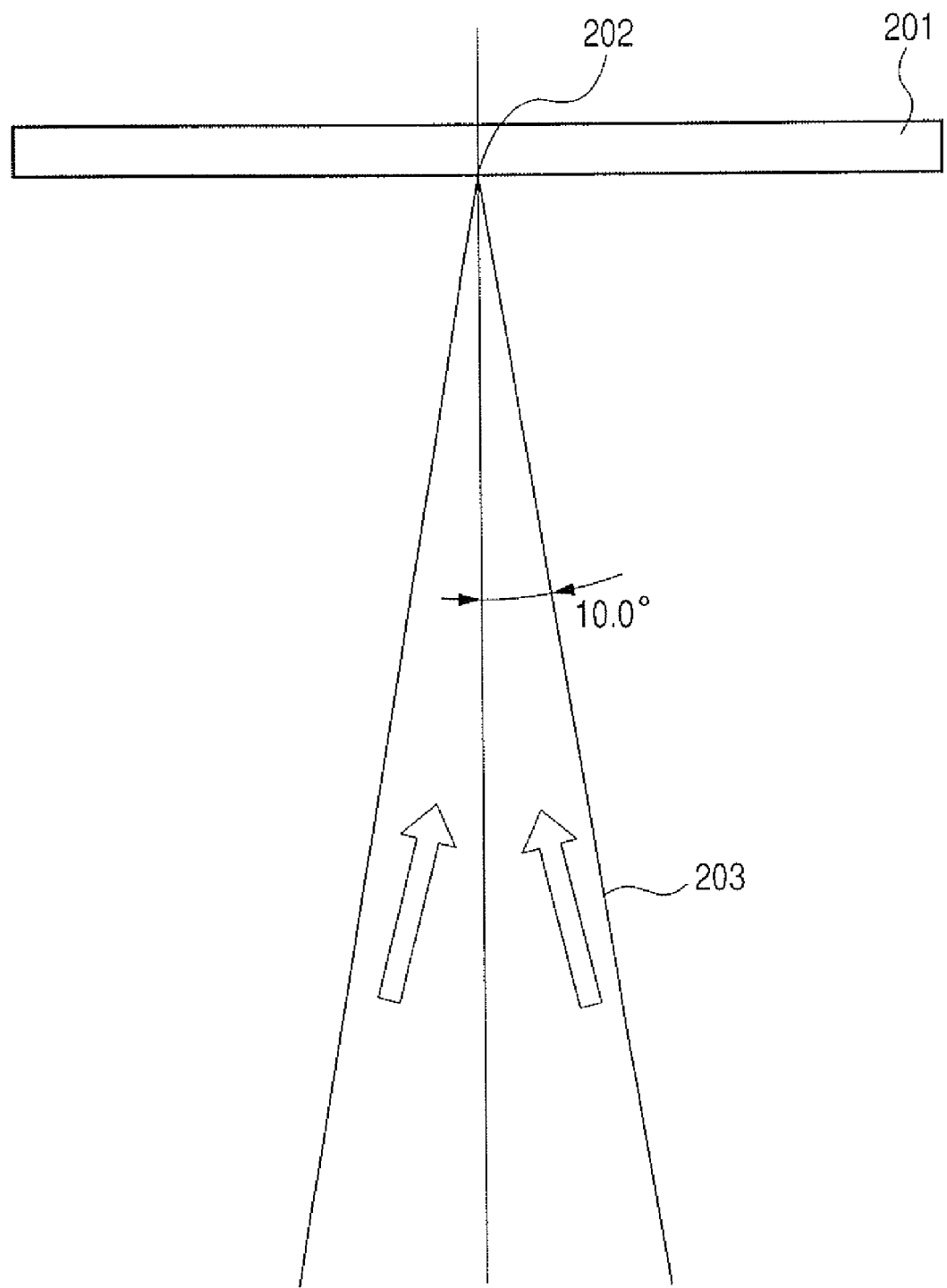
FIG. 2 is a principle explanatory diagram of a case of not applying the present invention.

This effect of the present invention will be described specifically using FIGS. 2 and 3 as examples. FIGS. 2 and 3 illustrate a substrate 201 and one point 202 of a metallic pattern-like element on the substrate 201. In addition, FIGS. 2 and 3 illustrate outermost parts 203 and 204 of an incoming beam, and a most inner part 205 of the incoming beam, respectively. Here, in order to describe a principle, one point on an element will be paid attention to and described. When an angle of light (incident light angle) which is incident into the metallic pattern 202 changes, a characteristic change as a change of a wavelength of the incident light occurs. That is, when an incident light angle becomes wide, a wavelength width of an absorption peak or a transmission peak by plasmon resonance generated in the metallic pattern spreads.

In order to prevent this, it is good to limit the incident light angle. On the other hand, when just the incident light angle is limited, the light use efficiency of a light source drops. An example in the case of limiting an incident angle and performing radiation will be illustrated in FIG. 2. FIG. 2 illustrates a state that detection light is radiated on metallic pattern-like particles at a narrow angle by an effective light source which has a strength center on an axis. On the other hand, FIG. 3 illustrates a radiation state of detection light by an effective light source (here, orbicular zone illumination), which has a strength center out of an axis, according to the present invention. In the example of FIG. 3, radiation is performed in an incident light distribution at a conical narrow angle that a half-vertical angle of an outer periphery is 45°. When respective light efficiencies are compared on a solid angle, it turns out that, in the case that an optical injection range is 10° as shown in drawings, the solid angle is about 0.09546 sr in radiation of FIG. 2, the solid angle is about 0.6030 sr in radiation of FIG. 3, and hence, the radiation of FIG. 3 is higher in the light use efficiency. In this way, a balance can be struck between limitation of an incident angle, and prevention of drop in light use efficiency by using the effective light source which has a strength center out of an axis.

Hereafter, exemplary embodiments of the system of the present invention will be described.

<Construction of Detecting Element>

A target detecting element used in the present invention will be described using FIGS. 4A, 4B, 4C, 4D, 4E, 4F, 4G and 4H. This detecting element has a substrate which has optical transparency, a metal thin film pattern provided on a surface of the substrate, and a target substance capturing body arranged on the metal thin film pattern.

As for the substrate, there is no limitation in particular so long as the substrate has optical transparency and has physical properties and characteristics for use for measurement. On this optically transparent substrate, anything is available so long as it is what has at least an optical transparency near any peak wavelength of absorption and transmission of light in the metal thin film pattern provided on the substrate.

As an example of the metal thin film pattern, what includes an array of dot shapes (an optical transparent substrate 301 and a metal thin film 302) as illustrated in FIGS. 4A, 4B, 4C and 4D can be cited. In addition, as another example of the metal thin film pattern, what has an array of pattern holes in a metal thin film (a metal thin film 302 and a hole 303 in the thin film) as shown in FIGS. 4E, 4F, 4G and 4H can be cited. In addition, as the form of a metal thin film dot and a pattern hole, as shown in FIGS. 4A, 4B, 4C, 4D, 4E, 4F, 4G and 4H, a circle, a square, a triangle, and a rectangle can be made, but the form is not limited to these. Size of the metal thin film dot or hole is sufficient so long as it is the size of enabling desired detection operation, and for example, it is desirable that a longest distance (for example, diameter in the case of a circle) between outer edges of planar shapes of the metal thin film dots and holes is about 20 nm to 500 nm.

Although a formation material of the metal thin film is sufficient to be a metal in which plasmon resonance can be observed, gold or silver, or an alloy including either or both of gold and silver is desirable. In addition, although the metal thin film may be formed directly on an optical transparency substrate, the metal thin film may be formed through a base layer such as Ti, Cr, or ITO. A film thickness of the metal thin film may be an extent that desired detection operation can be performed, and for example, it is good to make the film thickness 10 nm to 150 nm.

Furthermore, it is good to select a longest distance of a planar shape of the thin film dot or hole and a film thickness of a metal thin film selects so that their ratio may become 1:1 or less (direction where an aspect ratio is small).

It is sufficient that the target substance capturing body immobilized on the metal thin film pattern is just a substance which forms a specific bonding pair with a target substance. As suitable combinations of the specific bonding pair, an antigen/an antibody, complementary DNAs, a receptor/a ligand, and an enzyme/a substrate are cited, and when one side of each bonding pair is a target substance, another side or its analogue can become a capturing body. As such a target substance, biological materials (protein, nucleic acid, sugar chain, lipid, and the like), allergen, bacteria, virus, and the like are suitable.

<Detecting Apparatus Section>

Figure 1:
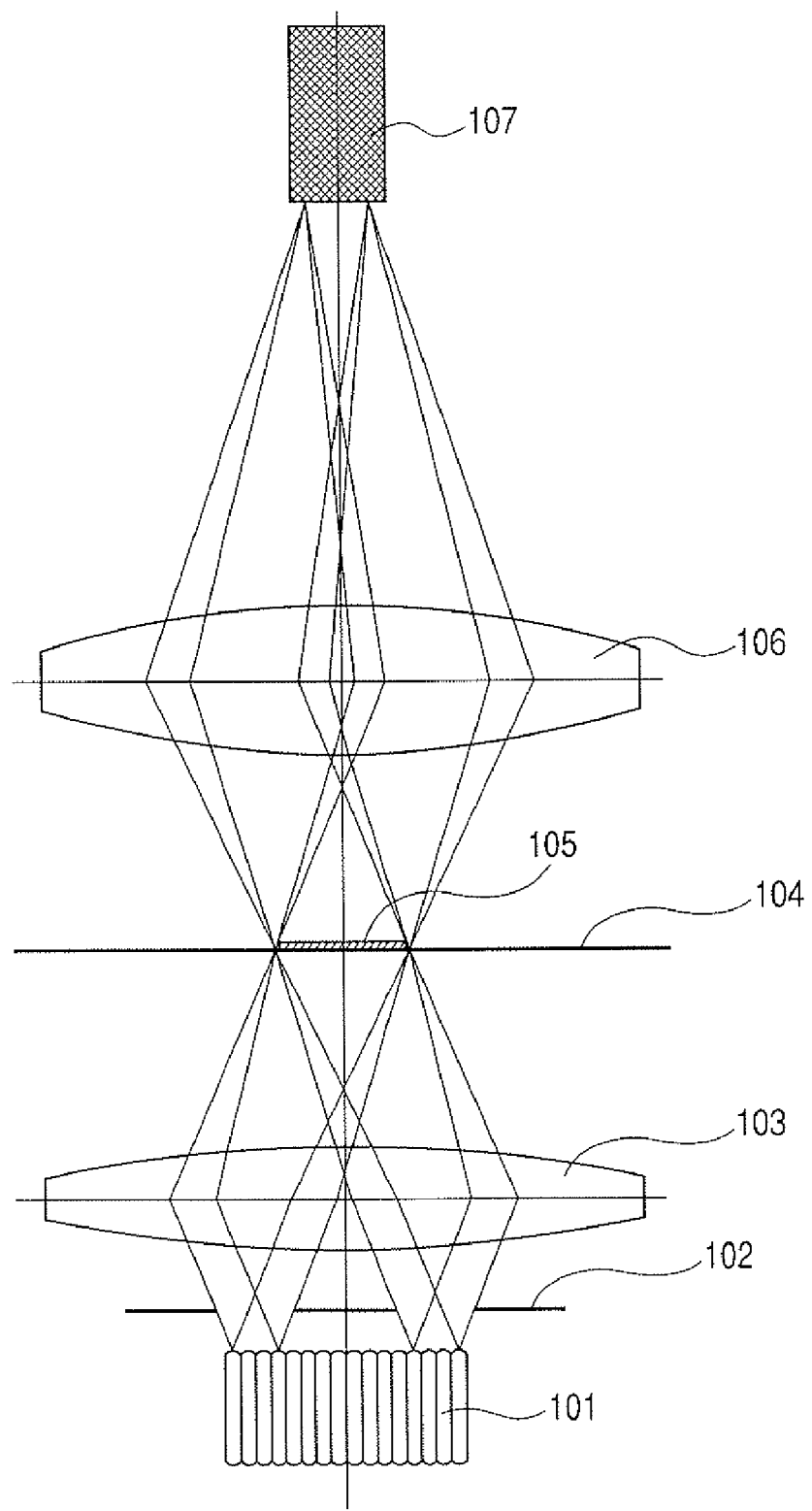
FIG. 1 is an optical system structural diagram of a detecting apparatus of the present invention.

An example of the target detecting apparatus of the present invention will be described using FIGS. 1, 5A, 5B, 5C, 5D, 5E, 5F and 5G. FIG. 1 illustrates a fly eye lens 101 for uniform illumination, an aperture 102 for determining an effective light source form, a form of which will be mentioned later, a condenser lens 103 for illuminating the detecting element, a substrate 104 of the detecting element, a metal thin film pattern section 105 of the detecting element, a condenser lens 106 in a light-receiving side, and a spectroscope light receiving section 107 which constructs a light receiving optical system. This spectroscope light receiving section is formed using an optical fiber in many cases.

Here, as forms of the aperture 102 for obtaining the effective light source form, forms illustrated in FIGS. 5A to 5G are suitable. In FIGS. 5A, 5B, 5C, 5D, 5E, 5F and 5G, a light shielding part 401 is filled with black, and a white-on-black section 402 is a transparent section.

Figure 5A:
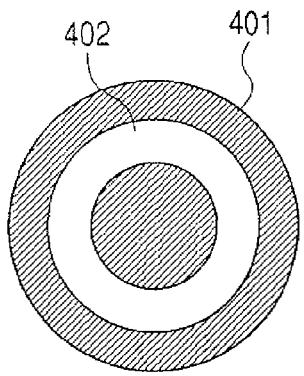
FIGS. 5A, 5B, 5C, 5D, 5E, 5F and 5G are examples of an aperture for an effective light source which can be used for the present invention.
Figure 5B:
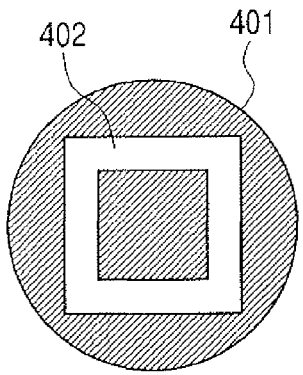
Figure 5C:
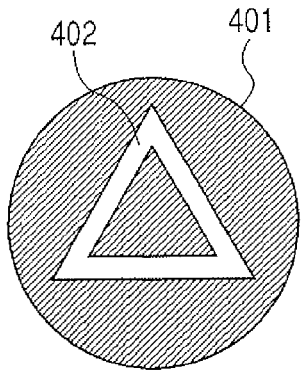
Figure 5D:
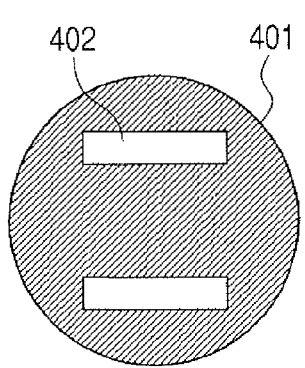
Figure 5E:
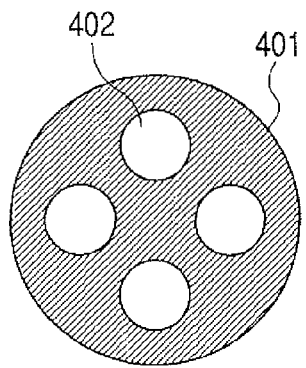
Figure 5F:
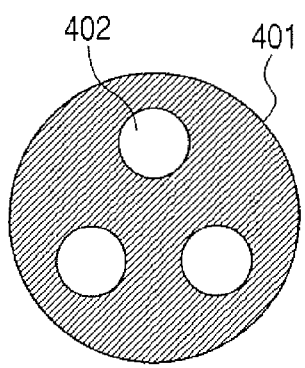
Figure 5G:
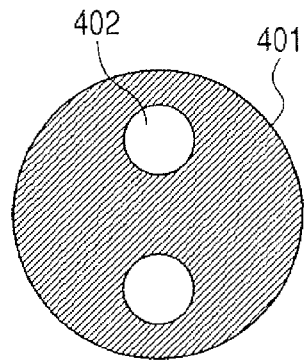

Here, relationship of the detecting element with the metal thin film patter will be described. In the case that the metal thin film dot and hole have forms which do not have anisotropy in a direction of a substrate plane as illustrated in FIGS. 4A and 4E respectively, it is good to use an aperture form without anisotropy as illustrated in FIG. 5A. In the case that the metal thin film dot and hole have squares with anisotropy as illustrated in FIGS. 4B and 4F, it is more desirable to select what have similar anisotropy as illustrated in FIGS. 5B and 5E. Similarly, it is suitable to select FIG. 5C or 5F for the forms illustrated in FIGS. 4C and 4G, and to select FIG. 5D or 5G for FIGS. 4D and 4H. According to the combinations of the aperture, metal thin film dot, and hole which are mentioned above, relationship between the plasmon resonance direction by the anisotropy of the detecting element and incident light angle distribution is further optimized. Therefore, the wavelength width of the absorption or transmission peak can be narrowed further. Here, when a form of a metal thin film pattern is a polygon, alignment of directions of the aperture, metal thin film dot, and hole is performed by aligning a position of a polygonal side or a vertex, and a position of a strength center of the aperture or a point where optical image height is specifically high, or a point where optical image height is specifically low.

The target substance detecting apparatus used in the present invention includes an illumination optical system, which has an effective light source which has a strength peak center out of the axis, as an illumination optical system, and a light receiving optical system corresponding to this illumination optical system, and the other portion can be constructed using publicly-known devices.

The target substance detection system of the present invention can be applied suitably as a sensor of various kinds of substances regardless of a medical application, industrial use, or home use.

Examples

Although the present invention is described below using examples, these never limit the scope of the present invention.
<Element Production Method>

The detecting element is produced by forming a gold thin film with 20 nm of film thickness on a quartz substrate with 0.725 mm of thickness by sputtering, and patterning this into any one of the predetermined patterns in FIGS. 4A, 4B, 4C, 4D, 4E, 4F, 4G and 4H using an electron beam lithography system. For example, the pattern in FIG. 4A is selected. The patterning is performed by etching in a state that a resist pattern is provided on a gold thin film. That is, a gold thin film is first covered with a resist, and patterning is performed using the electron beam lithography system into a form that the resist remains in positions corresponding to the form of the golden pattern in FIG. 4A. Here, although the electron beam lithography system is used, it is also sufficient to form a resist pattern using an X-ray lithography system or an excimer aligner. After resist formation, the gold in a resist removal section is etched by an ICP etcher. After etching, an asher removes the remaining resist, and the arrangement on the substrate with the gold thin film dots in FIG. 4A is obtained.

Here, although the method by etching is described, it is no matter to produce gold thin film dots by a lift-off method.

Figure 6:
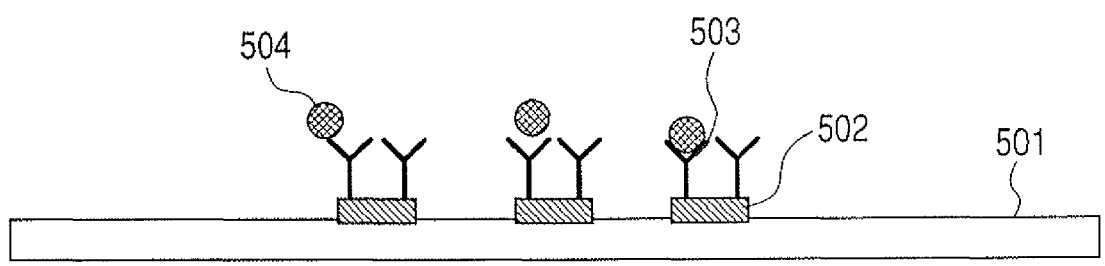
FIG. 6 is an imaged drawing after a reaction of the detecting element of the present invention.

Since the gold thin film pattern is formed up to here, a target substance capturing body is immobilized on this. An example of an immobilization method will be described with using FIG. 6. In addition, FIG. 6 illustrates a detection area at the time when a reaction at the time of detection is completed. In this example, a solid phase antibody 503 is immobilized in the detection area. For example, surfaces of the gold thin film dots are modified by dropping an ethanol solution of 11-Mercaptoundecanoic acid, which has a thiol group having high affinity with gold, on the gold thin film pattern. In the state, an N-Hydroxysulfosuccinimide (made by DOJINDO LABORATORIES) aqueous solution, and a 1-Ethyl-3-[3-dimethylamino]Propyl]carbodiimide hydrochloride (made by DOJINDO LABORATORIES) aqueous solution are added, which are incubated at room temperature for 15 minutes. Thereby, a succinimide group is exposed on surfaces of the gold thin film dots. In this state, for example, when an anti human CRP-mouse monoclonal antibody protein (made by Biogenesis) solution, which is capable of binding with human C-reactive protein, is dropped on the gold thin film pattern area by using a spotter and incubation is performed, the anti-human CRP-mouse monoclonal antibody is immobilized on the gold thin film dots 502. After the immobilization, if needed, it is sufficient to perform processing for inhibiting a nonspecific absorption reaction using a reagent with the inhibitory action of nonspecific absorption of bovine serum albumin, and the like. The detecting element can be produced by the above operations.

<Construction of Apparatus>

The target detecting apparatus of the present invention will be described using drawings. FIG. 1 illustrates a fly eye lens 101 for uniform illumination, and an aperture 102 for determining an effective light source form. Although forms as shown in FIGS. 5A, 5B, 5C, 5D, 5E, 5F and 5G are selectable as this aperture form, the orbicular zone illumination in FIG. 5A is selected here.

FIG. 5A illuminates a condenser lens 103 used for illuminating the detecting element, a substrate 104 of the detecting element, a metal thin film pattern section 105 of the element, a condenser lens 106 of a light-receiving side, and a spectroscope light receiving section 107. Here, this spectroscope light receiving section makes light be incident into an optical fiber here, and introduces the light into a spectroscope. Here, as detection light which is incident into the detecting element is incident from a position apart from an optical axis center as much as possible, light use efficiency becomes high. Nevertheless, it is necessary to pay attention to not exceeding a total reflection angle in an interface with the substrate of the detecting element. That is, it creates an optimal design position to set a boundary of an outermost aperture at a total reflection angle.

<Measurement Procedure>

Figure 7:
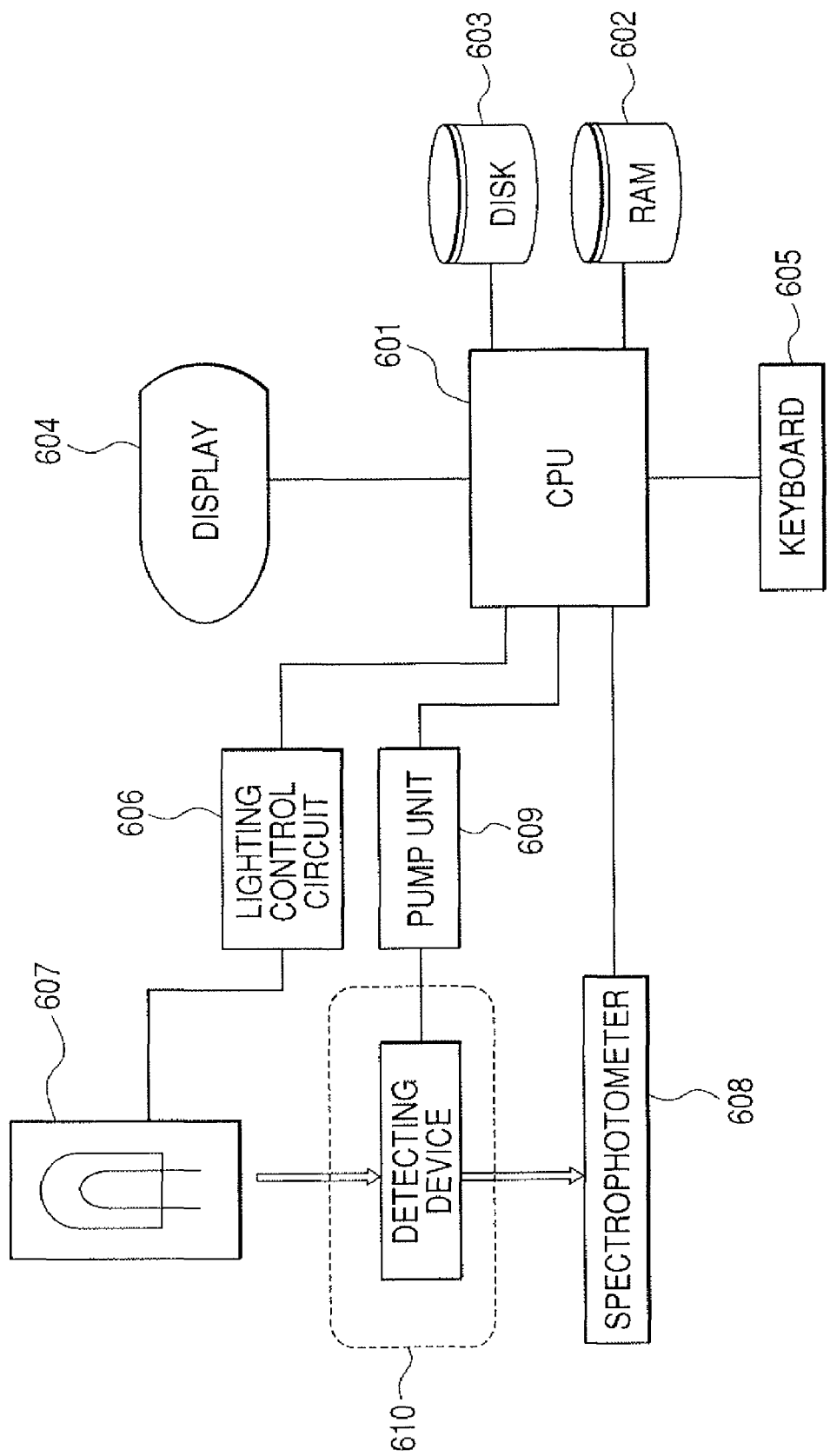
FIG. 7 is a block diagram of an example of apparatus structure of the detecting apparatus of the present invention.

FIG. 7 illustrates an example of a block diagram of a localized surface plasmon detecting apparatus of the present invention. First, a detecting element is arranged in a predetermined position in a flow path in a detecting element holding section 610.

Figure 8:
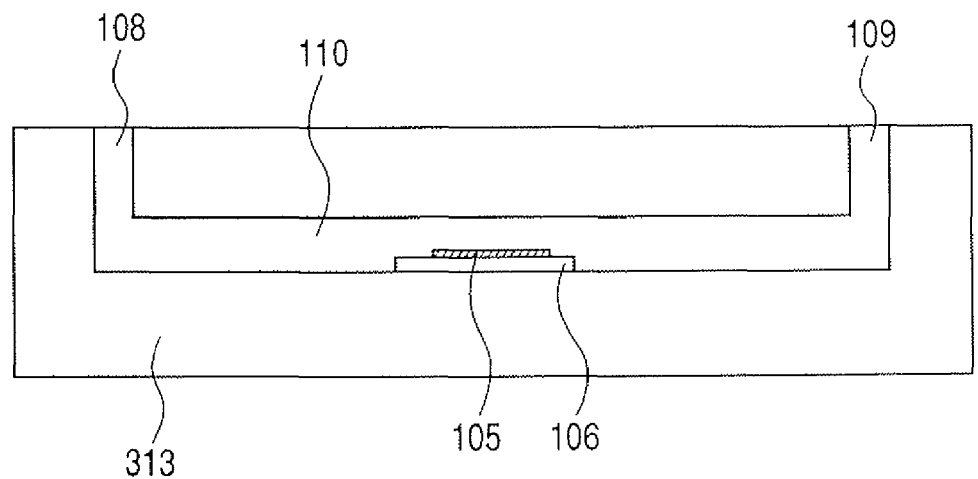
FIG. 8 is a schematic sectional view illustrating structure of a closed system of flow path.

This flow path may be either an open system or a closed system. FIG. 8 is a schematic sectional view illustrating a constructive example of the closed system of flow path. FIG. 8 illustrates a member 313 which has the flow path and a detecting element holding section, and the detecting element which has a metal thin film pattern 105 on a substrate 106 is arranged in a predetermined position in a flow path 110. There are apertures (108, 109) in an upstream edge and a downstream edge of this flow path to the exterior. By using these apertures, introduction of various liquids, such as a sample (liquid) and a cleaning liquid to an inside of the flow path 110 using a pump unit is possible. That is, in this system, a contact unit of the sample and detecting element is constructed by having at least the flow path and pump unit.

Explanation will be performed again using FIG. 7. Before contacting a sample with the detecting element, a light source 607 is turned on using a lighting control circuit 606. Here, a halogen lamp from which sufficient quantity of light is obtained in a wide band is used. An absorption spectrum before a reaction is acquired with a spectrophotometer 608. In addition, spatial arrangement of the light source 607, detecting element, spectrophotometer 608, and an optical system not shown is illustrated in FIG. 1. Then, an object sample is injected by a specified amount in a flow path with a pump unit 609, and is introduced into the detecting element holding section 610. Here, the sample including human CRP in unknown concentration is used. When incubation is performed for a fixed time after introduction, an antigen (here, human CRP) 504 is immobilized by the solid phase antibody 503 as illustrated in FIG. 6.

Then, an absorption spectrum after a reaction is acquired with the spectrophotometer 608 again.

In a concentration range in which a calibration curve can be created, an amount of antigens immobilized on the metal thin film dots depends on human CRP concentration in the original sample. When a capturing body captures a target substance as a detection object material, a refractive index near the metal thin film pattern changes. A rate of its change depends on an amount of human CRP captured by the antibodies on the metal thin film dot. That is, an absorption peak wavelength at the time of radiating detection light is shifted according to the refractive index, corresponding to the capture amount of human CRP, near the metal thin film pattern. Therefore, the amount of human CRP in the sample which corresponds to the amount of human CRP captured by the metal thin film dots is computable from this shift amount of the absorption peak wavelength on the basis of a calibration curve which was found beforehand using a sample whose concentration of the target substance (here human CRP) was known.

The system illustrated in FIG. 7 receives transmitted light supplied through the light receiving optical system in the spectrophotometer 608 as a spectrum measurement unit, and measures an absorption peak there. The absorption peak detected here is sent to a CPU 601, and is stored in memory (RAM) 602 if needed. The CPU 601 compares the input absorption peak with the calibration curve, which was stored beforehand, according to a program embedded beforehand, and calculates the amount of human CRP in the sample. The calculated amount of human CRP may be displayed on a display 604 if needed. In addition, it is also good to record a program for measurement in a disk 603, to load the program into the RAM 602, and to execute a detection operation. In addition, these operations can be controlled using a keyboard 605.

In addition, a unit to acquire respectively spectroscopic characteristics before and after contacting a sample with the detecting element can be further provided in this system. For example, it is also good to program the process, and to adopt such structure that the CPU 601 may perform an instruct so as to perform automatically measurement of spectroscopic characteristics before and after contacting a sample with the detecting element with interlocking with a sample solution sending operation of a pump unit.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-078793, filed Mar. 22, 2006, which is hereby incorporated by reference herein in its entirety.

What is claimed is:

1. A target substance detection system for detecting a target substance in a sample, comprising:
    (1) a detecting element for detecting a target substance which is comprised of:
        a substrate optically transparent,
        a metal thin film pattern formed on the substrate, and
        a target substance capturing body immobilized on the metal thin film pattern; and
    (2) a target substance detecting apparatus which is comprised of:
        an illumination optical system for irradiating the detecting element with a wideband detection light comprised of an effective light source which has a center of a strength peak out of an axis,
        a light receiving optical system which condenses light passed through the detecting element when the detecting element is irradiated with the detection light,
        a unit for taking a spectrometric measurement of light condensed by the light receiving optical system,
        a unit for bring a sample into contact with the detecting element, and
        a unit for computing an amount of the target substances captured on the detecting element from a difference between spectroscopic properties before and after the contact of the sample with the detecting element.

2. The target substance detection system according to claim 1, wherein a form of the effective light source has the same anisotropy as the anisotropy of the metal thin film pattern.

3. The target substance detection system according to claim 2, wherein a form of the effective light source is made to be changeable at any time according to the anisotropy of the metal thin film pattern.

4. The target substance detection system according to claim 1, wherein
    an incident angle of light which is incident into the detecting element from a position most apart from an optical axis center in a distribution of the effective light source is a total reflection angle on the substrate.

* * * * *